United States Patent [19]

Berstein et al.

[11] Patent Number: 4,780,613
[45] Date of Patent: Oct. 25, 1988

[54] INFRARED SPECIES SPECIFIC EMISSION SOURCE

[75] Inventors: Lawrence S. Berstein, Bedford; Michael W. Matthew, Burlington; Fritz Bien, Concord, all of Mass.

[73] Assignee: Spectral Sciences, Inc., Burlington, Mass.

[21] Appl. No.: 909,706

[22] Filed: Sep. 22, 1986

[51] Int. Cl.[4] .............................................. H01J 65/04
[52] U.S. Cl. .................................... 250/343; 250/493.1
[58] Field of Search ............. 250/504 R, 495.1, 493.1, 250/343, 339; 313/594, 601

[56] References Cited

U.S. PATENT DOCUMENTS

| 3,751,666 | 8/1973 | Hug ................................. 250/495.1 |
| 4,197,466 | 4/1980 | Hug ................................. 250/495.1 |
| 4,641,973 | 2/1987 | Nestler et al. ....................... 356/418 |

Primary Examiner—Janice A. Howell
Assistant Examiner—Constantine Hannaher
Attorney, Agent, or Firm—Joseph S. Iandiorio; William E. Noonan

[57] ABSTRACT

An infrared species specific emission source which includes a closed container having at least one transparent portion for containing at least one specific molecular species. The molecular species within the container is heated sufficiently to cause the species to emit a characteristic infrared spectal emission through the at least one transparent portion of the container to the infrared instrument.

20 Claims, 10 Drawing Sheets

INFRARED SPECIES SPECIFIC EMISSION SOURCE

FIELD OF INVENTION

This invention relates to an infrared species specific emission source and in particular to a source which heats a single molecular species sufficiently to cause it to emit its characteristic infrared emission spectrum for use, for example, in spectral analysis of target samples.

BACKGROUND OF INVENTION

Conventional infrared emission sources typically employ a wire, metal or ceramic element which is heated to emit a continuous broad band of infrared radiation. However, such infrared sources exhibit a number of difficulties, particularly when they are employed for monitoring the presence of trace molecular species in a target gas sample. In such monitoring systems the concentration of the trace species being monitored is typically determined as a function of the amount of infrared radiation absorbed by the species in characteristic wavelength bands. Because the molecular species present in the sample absorbs radiation in these bands, the resultant reduction in the intensity of the infrared output signal in the bands is measured and used to determine the presence or concentration of the species in the sample.

The sensitivity achieved by systems employing conventional infrared emission sources is sometimes rather poor. This occurs for molecular species where the average spacing of the absorption lines is significantly larger than the average width of the lines. In these instances only a small fraction of the total broad band radiation will be absorbed within the molecular absorption lines. This problem is particularly troublesome at low concentrations of the trace species. Even though infrared filters are used to provide the characteristic absorbed wavelength bands to the sample, these introduced bands are still fairly broad relative to the absorbing linewidths within these bands of the trace species at low concentrations. As a result, the output signal from the sample is comparable in strength to the introduced signal. To determine the trace species concentration the introduced and output signals must be compared and because at low concentrations both are relatively strong signals, such comparison is difficult. Detection has been facilitated somewhat by increasing absorption to reduce the intensity of the sample output signal. However, this has typically required an increased sample path length achieved by employing relatively large, complex and cumbersome multiple reflection optical cells.

Selectivity is also a significant problem because the introduced wavelength bands are fairly wide. Species other than the test species may also absorb in those wavelength bands and therefore the resultant reduction in the output signal may be due in part to the presence of species other than the particular trace species being monitored. Such systems are often not able to distinguish between various species present in the sample and as a result erroneous measurements may be taken.

In an attempt to overcome the selectivity problem, gas correlation spectroscopy has been employed. Therein a first beam of a continuous band of infrared emission is passed through a gas sample containing a trace species, for example HCl, to be monitored. The output signal from this beam indicates absorption by the trace species as well as other impurities which absorb in the same region. At the same time a second beam of the broad band is passed through a filter containing a known amount of just the trace species being monitored. The output from this filter is a signal whose strength is reduced only by the absorption by the trace species. This signal is then passed through the sample where it is further reduced by both the trace species and the impurities in the sample. The two output signals from the sample are then compared and because the reductions due to impurities cancel out, the difference in the signals is due entirely to the presence of the trace species in the sample.

Although gas correlation spectroscopy does improve selectivity somewhat it still requires that two fairly strong signals be compared. Therefore, sensitivity at low concentrations continues to be a problem. Moreover, these systems are unwieldy and require the manufacture and use of a special molecular species filter for each species being monitored.

SUMMARY OF INVENTION

It is therefore an object of this invention to provide an infrared species specific emission source which greatly reduces continuum infrared emission and generally provides just the line emission of the molecular species of interest.

It is a further object of this invention to provide an infrared species specific emission source which is particularly suited for use in an infrared instrument for measuring the presence of a gas phase molecular species.

It is a further object of this invention to provide an infrared species specific emission source which results in enhanced sensitivity and which eliminates the need for broad band and molecular species filters and large cumbersome optical cells.

It is a further object of this invention to provide an infrared species specific emission source which permits of a more simple, compact and inexpensive detection system.

It is a further object of this invention to provide an infrared species specific emission source which efficiently maintains an even temperature level.

This invention results from the realization that in certain spectral analysis applications the infrared line emission spectrum of a single specific molecular species may be utilized to provide greatly improved results over a continuous broad band infrared emission spectrum and that such a line spectrum may be produced by heating a closed container of the molecular species of interest to the temperature necessary for it to emit infrared radiation at its characteristic wavelengths.

This invention features an infrared species specific emission source for a infrared instrument detection system which includes a closed container having at least one transparent portion for containing at least one specific molecular species corresponding to the species to be detected. There are means for heating the molecular species within the container sufficiently to cause the species to emit a characteristic infrared spectral emission through the at least one transparent portion of the container to the infrared instrument.

In a preferred embodiment the emission source includes a housing for receiving the container and the means for heating. The housing may include insulation means for reducing heat loss from the container and such insulation means preferably includes insulating material which surrounds at least a portion of the container and the means for heating. The insulation means may also include a transparent convective insulating element spaced from a transparent portion for transmitting the spectral emission therethrough. The container may include a combination of molecular species.

Means may be provided for maintaining the source at a substantially constant operating temperature and the housing may include heat dissipating means for maintaining the source at such a temperature. The means for heating may include a heating element disposed about the container and means may be attached to the insulating material for mounting such a heating element about the container. The means for mounting typically includes a potting compound in which the heating element is embedded.

This invention is also directed to an emission source/target sample system for a infrared instrument detection system which includes a sample path for containing a sample to be monitored for one or more selected molecular species. There are means for providing to the sample path an infrared source spectral emission which corresponds to an absorption spectrum of the molecular species to be monitored. It is preferred that the means for providing include an emission source as described above.

DISCLOSURE OF PREFERRED EMBODIMENT

Other objects, features and advantages will occur from the following description of a preferred embodiment and the accompanying drawings, in which:

FIG. 10G illustrates for FIG. 10E the variation in output intensity with variation in concentration.

Figure 1:
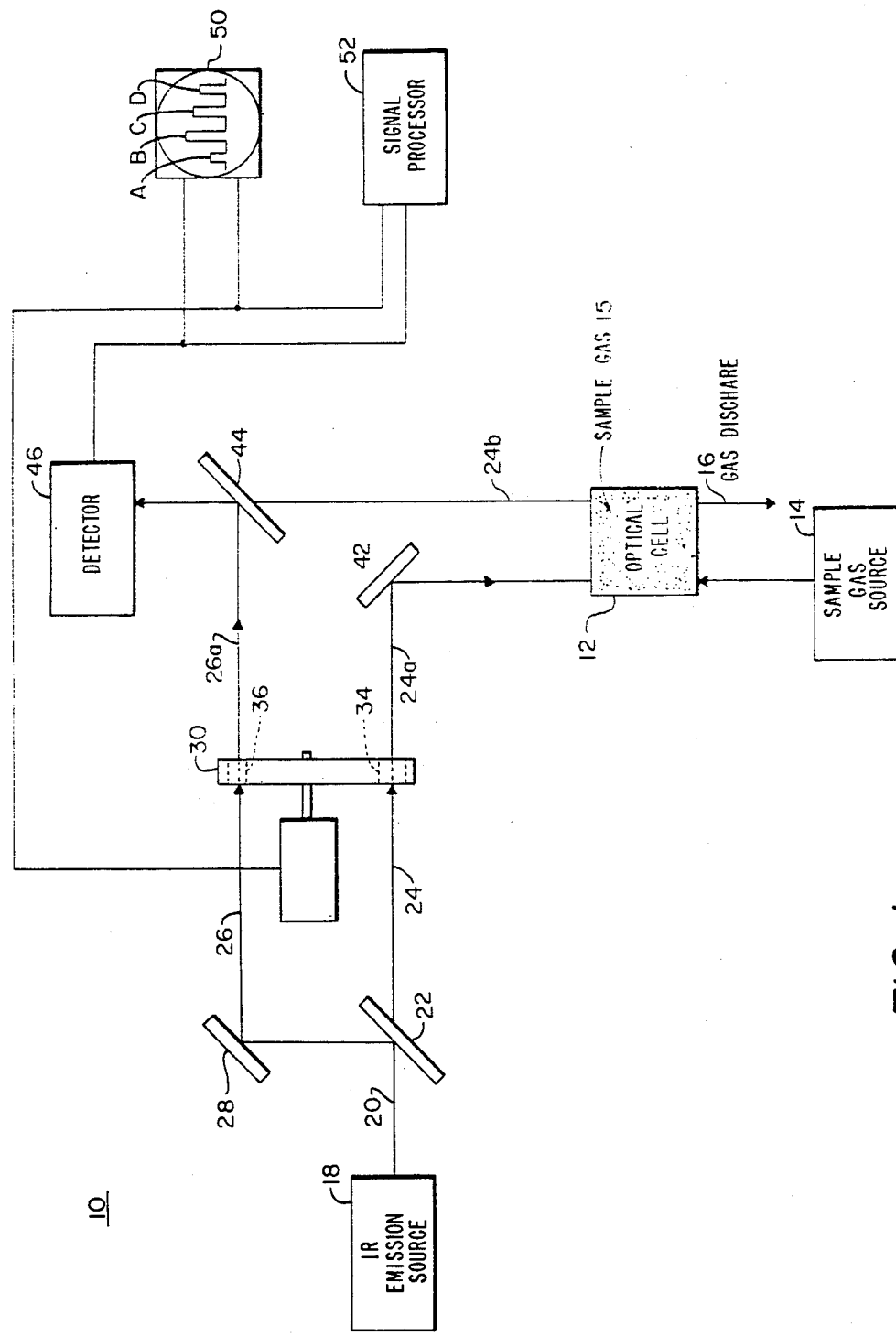
FIG. 1 is a schematic view of an infrared gas phase molecular species monitor employing the infrared species specific emission source of this invention.

An infrared species specific emission source according to this invention may be accomplished by providing a closed container or cell having at least one transparent portion, e.g., window, for containing one or more specific molecular species corresponding to the molecular species to be monitored and means for heating the molecular species within the container sufficiently to cause that species to emit its characteristic infrared emission spectrum through one or more transparent portions of the container. It should be understood that although purely the molecular species of interest may be present in the emission source, more often that molecular species is mixed with and diluted by a relatively inert gas such as argon or nitrogen which does not emit radiation that is significantly absorbed in the spectral regions of interest. A preferred container includes very thin (e.g., approximately 0.5 mm) windows composed of water-free quartz or sapphire having a low emissivity to reduce the emission of a continuum broad band of infrared radiation. The molecular species within the cell is heated by, for example, a wire wound about the emission cell. The wire may be composed of an iron-chromium-aluminum-cesium alloy or other comparable material and typically is resistively heated by current from a battery or small generator. The emission cell and heater element are typically mounted within a housing which may be constructed of black anodized aluminum having exterior cooling fins to dissipate heat generated by the emission source. To further regulate heat loss from the emission source, insulation, such as ceramic fiber or similar material may be provided between the container and the housing. One or more openings are provided through the insulation and the housing to transmit the infrared radiation emitted by the heated gas within the container. To prevent excessive convective heat loss this opening may be covered by an insulating window composed of sapphire or a similar material with low emissivity. The wire heater may be mounted to the inner surface of the ceramic insulation by a potting compound or equivalent means.

A preferred application for this infrared source is in an infrared instrument for detecting one or more gas phase molecular species such as HCl, $H_2O$ vapor, hydrocarbons, $NO_2$, $NO_3$, CO, $CO_2$ and other species, alone or in combination, in a sample path containing a sample to be monitored for the molecular species. At least one primary, e.g. absorbing, spectral emission line of the characteristic spectral emission provided by the emission source of this invention is passed through the sample path. As used herein the terms "absorbing" and "nonabsorbing" are not absolute but, rather, should be understood to refer to regions of radiation which are significantly absorbed and significantly nonabsorbed, respectively, by the gas in the sample path. The decrease in the intensity of one or more of the absorbing infrared source spectral emission lines passed through the sample path is detected as a function of the absorption of those lines by the molecular species present in the sample. The level of such absorption is similarly a function of the presence and concentration of the molecular species in the sample.

There is shown in FIG. 1 a preferred infrared instrument detection system utilizing the emission source of this invention. The system comprises an infrared monitor 10 which includes an optical cell 12 into which is introduced from source 14 a sample gas 15 to be monitored for one or a combination of molecular species of interest. When the monitoring of the sample gas has been accomplished as described below the gas is discharged from the cell as indicated by arrow 16. The flow of sample gas 15 into and out of optical cell 12 may be either periodic or continuous. Cell 12 may include a multiple reflection optical cell such as a White cell or an optical cell employing only a single reflection or a single pass with no reflections whatsoever.

An infrared emission source 18, according to this invention, provides an infrared source emission 20 of the molecular species to be monitored. Emission 20 includes one or more primary or absorbing emission lines which are significantly absorbed by the molecular species being monitored in the sample gas and at least one secondary or nonabsorbing emission line which is not significantly absorbed by the molecular species. Emission 20 is split by beam splitter 22 into a sample beam 24 and a reference beam 26. Sample beam 24 is directed by beam splitter 22 and reference beam 26 is directed by beam splitter 22 and mirror 28 toward chopper wheel 30.

Figure 2:
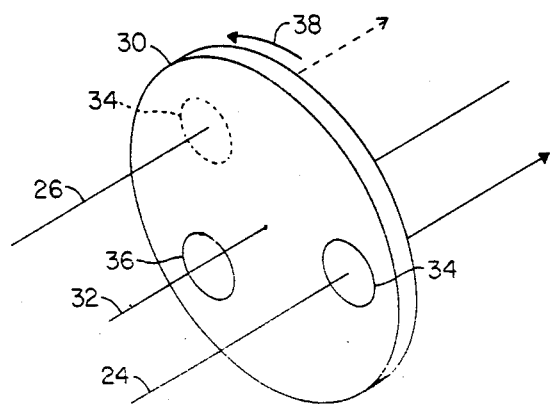
FIG. 2 is a simplified axonometric view of the chopper wheel and the sample and reference beams of infrared radiation.
Figure 3:
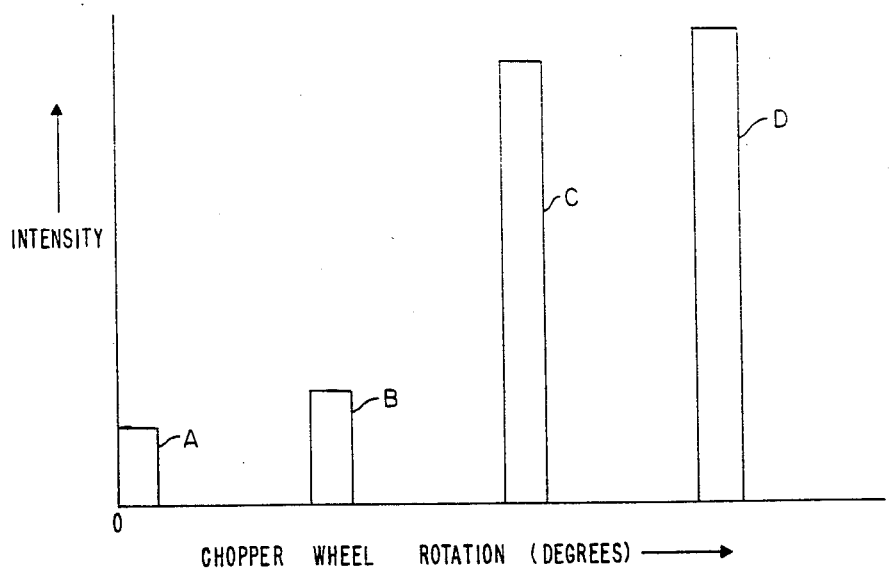
FIG. 3 is a graph illustrating the detected output and reference (emission line) intensities versus the position of the chopper in FIG. 1.

The chopper wheel, further shown in FIG. 2, is rotatable about an axis 32 and selectively transmits both sample beam 24 and reference beam 26. Chopper 30 includes a first filter 34 which transmits only the absorbing emission lines of infrared radiation and a second filter 36 which transmits only the nonabsorbing emission lines of the infrared radiation. Chopper wheel 30 is rotated in the direction of arrow 38 so that filters 34 and 36 are alternately passed through both sample beam 24 and reference beam 26. For example, in FIG. 2 first filter 34 is shown passing through sample beam 24. This causes the absorbing emission lines of infrared radiation to be transmitted through the filter. As indicated by arrow 24a, FIG. 1, the sample beam is then directed by mirror 42 into optical cell 12 so that it passes through the sample gas 15 in cell 12. After passing one or more times through the sample gas 15, the absorbing emission lines exit cell 12 as beam 24b and are transmitted through a beam splitter 44 and their intensity A, FIG. 3, is sensed by a detector 46. While sample beam 24 is being transmitted through filter 34, chopper wheel 30 blocks transmission of reference beam 26 and, as a result, the intensity of that beam is not measured.

The chopper wheel continues rotating in the direction of arrow 38, FIG. 2, and after one-quarter turn, i.e., at the 90° position, first filter 34 is at the position indicated in phantom. The absorbing emission lines of the reference beam 26 are then transmitted through filter 34. The transmitted portion 26a, FIG. 1, of the reference beam is reflected by beam splitter 44 and sensed by detector 46. At the same time, transmission of sample beam 24 is blocked by chopper 30 and, as a result, only the intensity B, FIG. 3, of the absorbing emission lines of the reference beam is measured.

An additional one-quarter turn of the chopper wheel to the 180° position places filter 36 in the path of sample beam 24. Accordingly, the nonabsorbing emission line or lines of the sample beam are transmitted through the chopper and passed through optical cell 12. The output intensity C, FIG. 3, of the one or more nonabsorbing emission lines of the sample output beam 24b, FIG. 1, are then sensed by detector 46. Filter 36 is finally rotated through the path of reference beam 26 to the 270° position so that the intensity D of the nonabsorbing emission lines of the reference beam may be similarly detected.

With each revolution of chopper 30 detector 46 successively senses the intensities of the absorbing emission lines and the nonabsorbing emission lines of the sample output beam 24b and the reference beam 26a. Between each quarter turn the sample and reference beams are blocked by the chopper and no infrared intensity is detected.

Following detection of the four intensities A, B, C and D, those intensities may be displayed, for example, on an oscilloscope 50 and they are provided to a signal processor 52 where they are processed, as described more fully below, to determine the concentration of the molecular species in the gas sample.

Although chopper 30 is shown, in FIG. 1, transmitting the sample beam before it is passed through optical cell 12 in alternative embodiments the chopper may be arranged after the cell and transmit sample output beam 24b. In addition, if source or filter drift can be tolerated then the reference beam 26 may be omitted. For example, source and detector drift could be compensated for by a third nonabsorbing band.

Figure 4:
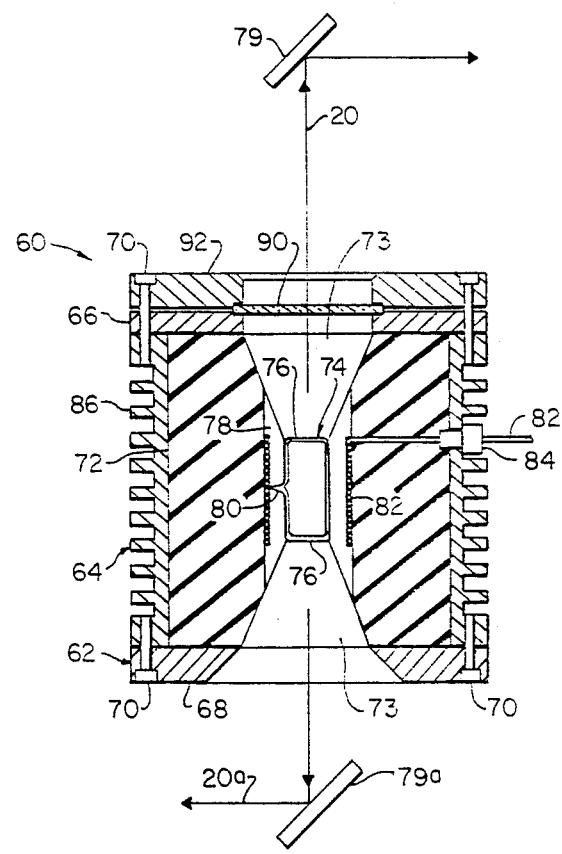
FIG. 4 is a cross sectional view of a preferred infrared species specific emission source according to this invention.

A preferred emission source 60 for providing the absorbing and nonabsorbing emission spectral lines while at the same time largely eliminating the broad band continuum infrared emission is shown in FIG. 4. The emission source includes a housing 62 having a peripheral jacket 64 and end plates 66 and 68 which are secured to jacket 64 by screws 70. An insulation member 72 is mounted within housing 62 and a central axial opening 73 is formed through housing 62 and insulation member 72. A sealed container or emission cell 74 having end windows 76 is disposed longitudinally within opening 73 and is secured to insulation member 72 by potting compound 78. In particular, emission cell 74 may include a projection 80 which is formed when cell 74 is blown or otherwise constructed. The emission cell contains the gas phase molecular species being monitored plus a relatively inert gas which does not emit infrared radiation in the wavelength regions absorbed by the sample gas. For example, if gas sample 15 is being monitored for HCl, cell 74 may be filled, for example, to a pressure of one-third atmosphere with a mixture of nitrogen and HCl. A resistively heated wire heating element 82 is introduced through a ceramic feedthrough 84 into the housing. Element 82 extends through insulation member 72 and is embedded in potting compound 78 and disposed about emission cell 74.

Emission source 60 is operated by employing a battery or generator or similar means, not shown, to energize heater element 82. The molecular species within cell 74 is heated sufficiently by element 82, for example to 1000° K., to emit its characteristic infrared emission spectral lines. This emission exits cell 74 through windows 76 and exits emission source 60 through opening 73. The emission source is held by a support structure, not shown, and is arranged with opening 73 disposed vertically so that free convection does not excessively cool the lower window 76 of cell 74. The upwardly emitted infrared radiation 20 is then redirected by a mirror 79 and split into reference and sample beams as described in connection with FIGS. 1 and 2. At the same time, the downwardly emitted radiation 20a is directed by a mirror 79a away from the optical path of emission 20.

Emission source 60 includes a number of features which permit its temperature to be maintained at a substantially constant level. For example, cooling fins 86 are provided on the exterior of jacket 64 so that heat is dissipated uniformly from the emission source. Housing 62 is also constructed from a material such as black anodized aluminum which efficiently dissipates the heat generated by heater element 82. On the other hand, insulation member 72 prevents the heat from being dissipated too rapidly from the emission source and helps maintain the temperature at a substantially constant level. Convective heat loss through opening 73 is further reduced by an insulating window 90 which is mounted over the top of opening 73 and held in place by a retainer 92 attached to jacket 64 by screws 70. Because only a small portion of the surface area of cell 74 is exposed, i.e., windows 76, radiative losses from cell 74 are minimized; yet an effective aperture for the radiation is provided through opening 73. Both the window 76 and window 90 are composed of a low emissivity substance such as quartz or sapphire. This greatly reduces the intensity of the continuum infrared spectrum which may be emitted by these elements. As a result, substantially all of radiation 20 consists of the infrared spectral emission lines of the molecular species within cell 74.

Figure 5A:
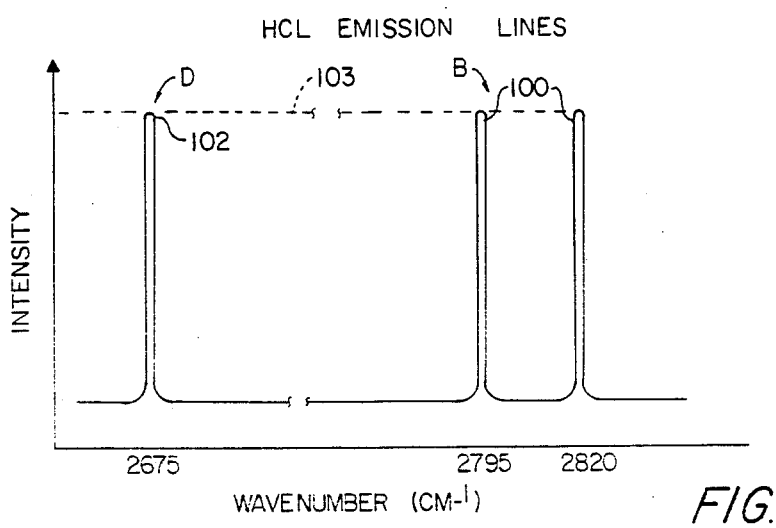
FIG. 5A illustrates representative primary and secondary emission lines from an HCl emission source.

Because detector 46, FIG. 1, is detecting the intensity of only the infrared source spectral emission lines, and not a broad band continuum of infrared radiation, measuring the absorption of the infrared emission by the molecular species in question is facilitated. As shown in FIG. 5A, where the molecular species of concern is HCl, beam 20 includes absorbing emission lines 100 centered on the wavenumbers 2795 and 2820 cm$^{-1}$ respectively. The sample beam also includes a nonabsorbing emission line 102 centered on the wavenumber 2675 cm$^{-1}$. Additional emission lines are not shown for clarity. These spectral lines are transmitted in both sample beam 24 and reference beam 26 of FIG. 1. However, when chopper 30 passes filter 34 through beam 24 only lines 100 are passed through to the optical cell. Conversely, when filter 36 is passed through the sample beam, only line 102 passes through to the optical cell. Similarly, lines 100 and line 102 are selectively transmitted as the reference beam 26 engages the respective filters of the chopper.

As emission lines 100 and 102 alternately pass through the gas in the optical cell their intensity is reduced to the extent that the emission lines are absorbed by the molecular species (HCl) present in the gas sample. As indicated by absorption line 104, FIG. 5B, the molecular species in the sample significantly absorbs infrared radiation which corresponds in wavelength to the absorbing emission lines passed through the gas. The size of lines 104 varies according to the amount of molecular species in the sample. As further indicated by absorption line 106 the HCl in the sample does not substantially absorb radiation corresponding in wavelength to the nonabsorbing emission line 102. As a result of the absorption of the absorbing emission lines 100 by the molecular species in the gas sample, intensity of the output absorbing emission lines 100a, FIG. 5C, is significantly reduced. Whereas the absorbing emission lines provide an intensity signal B (e.g., the reference intensity), prior to introduction to the optical cell, their output intensity is reduced to A. At the same time because nonabsorbing emission line 102 is absorbed by only an insignificant amount, the intensity of the nonabsorbing emission line 102b which exits the optical cell is reduced only slightly from D to C. By detecting the decrease in the intensity of the absorbing emission lines the level of absorption by the molecular species being tested and, hence, the concentration of that species in the sample can be determined as described more fully below.

Figure 5B:
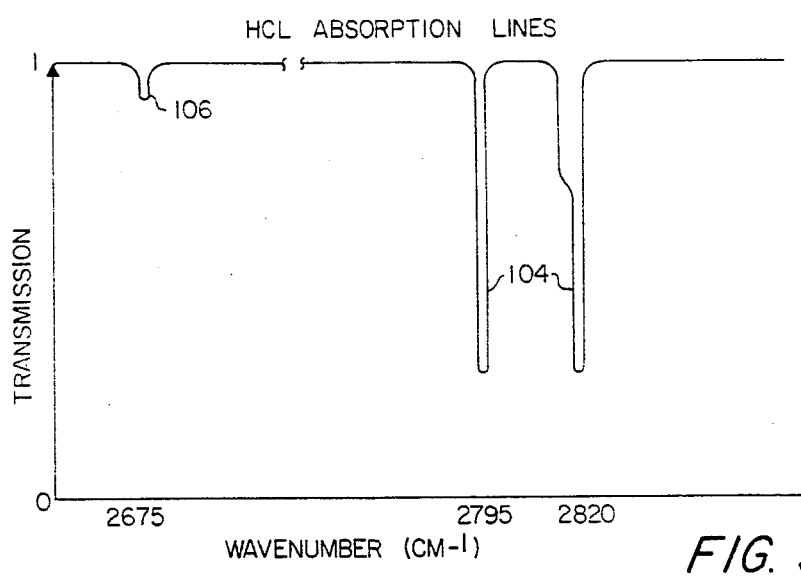
FIG. 5B illustrates a representative transmission spectrum for the primary and secondary emission lines of HCl.
Figure 5C:
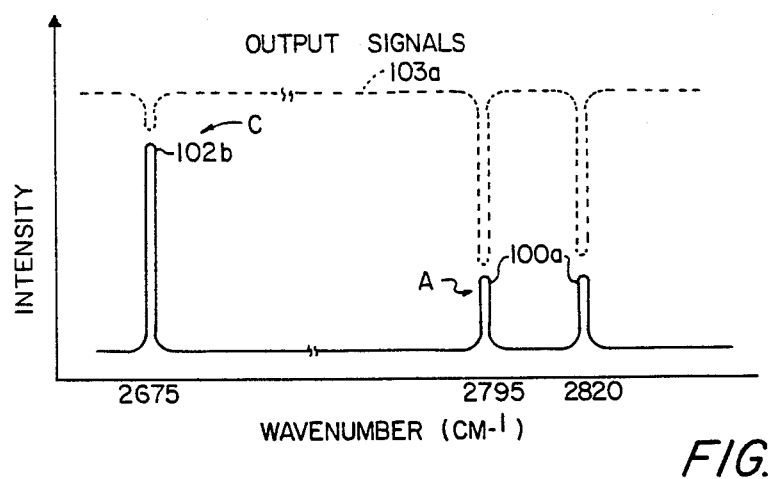
FIG. 5C illustrates a representative output intensity at the detector of FIG. 1.

In contrast to the system of this invention, when a broad band continuum infrared source is employed, a broad band 103, FIG. 5A, is absorbed to the extent of absorption lines 104, FIG. 5B and the intensity of its output signal 103a, FIG. 5C, remains relatively large compared to that of the initial signal 103. As a result, the decrease in intensity, and hence the absorption and concentration of the molecular species in the sample, are quite difficult to monitor, particularly at low concentrations where the intensity decrease may be negligible. Moreover, species other than the species being monitored may absorb a portion of the broadband sample beam and as a result provide misleading indications of absorption and erroneous determinations of concentration. The present invention alleviates these difficulties: even small reductions in the intensity of absorbing lines 100 are detectable, being compared to a smaller emitted intensity, and absorption by irrelevant species with neighboring absorption lines is avoided.

Figure 6:
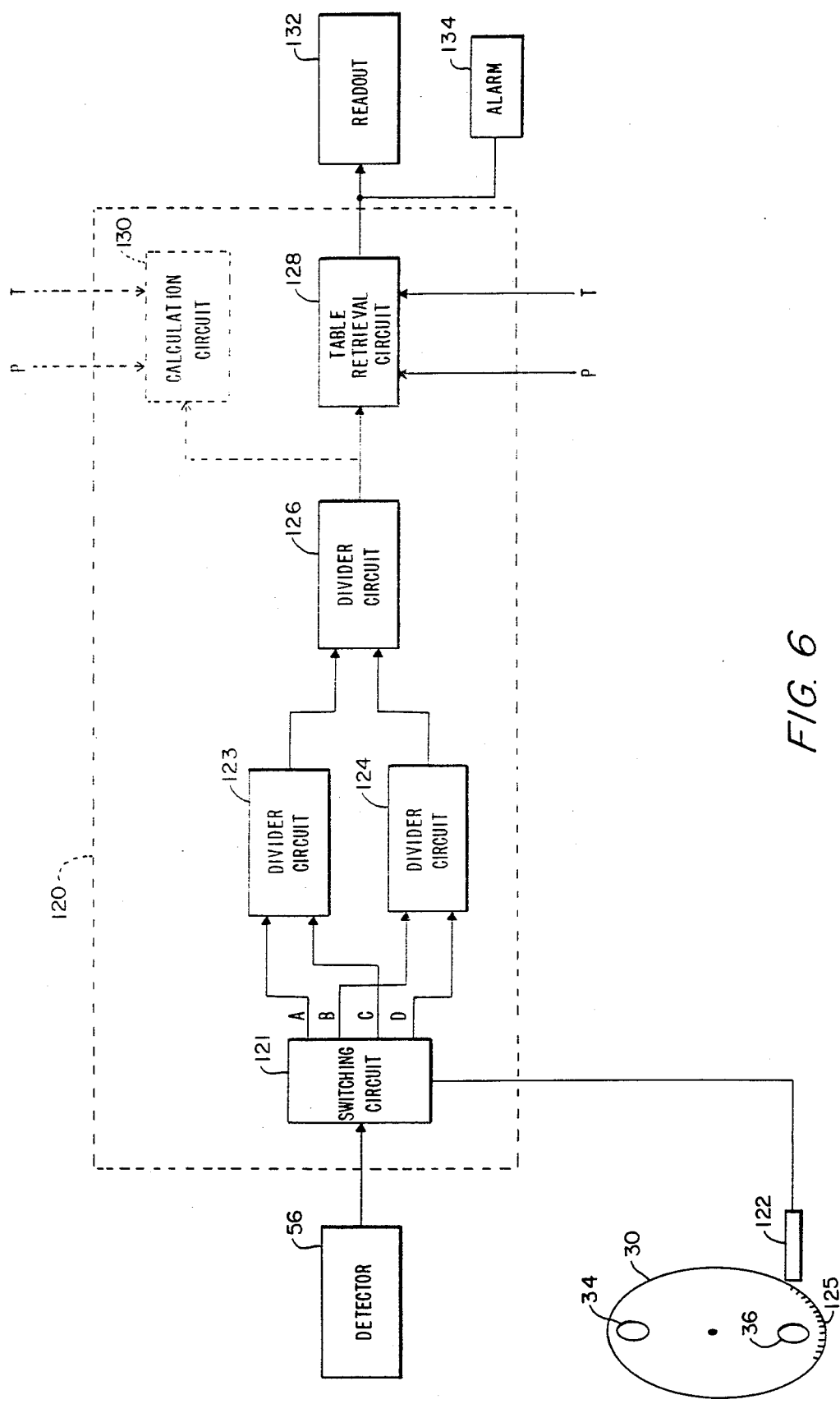
FIG. 6 is a schematic view of a signal processor for normalizing and comparing the sensed detector intensities and for determining the molecular species concentration and a circuit for sensing the location of the chopper device.

A signal processor 52 for processing the detected intensity signals A, B, C and D is shown in FIG. 6. The respective signals are provided from detector 46 to a switching ciruit 121. A sensor 122 detects appropriate indicia 125 disposed around the circumference of wheel 30 and provides a signal to circuit 121 which identifies the signal received from detector 46 as either signal A, B, C or D. The switching circuit feeds signals A and C, respectively representing the intensities of the absorbing and the nonabsorbing emission lines of the sample output beam 24b, to divider circuit 123 where they are divided to provide normalized signal A/C. Similarly, signals B and D, representing the intensities of the absorbing and nonabsorbing emission lines, respectively, of the reference beam, are provided by switching circuit 121 to a divider circuit 124 where they are divided to yield the normalized signal B/D. Signals A/C and B/D are divided in a divider circuit 126 to yield signal R (e.g., $(A \times D/(B \times C))$). Signal R is provided along with signals indicative of the temperature T and the pressure P of the fluid of the sample to a table retrieval circuit 128 where the proportion of HCl or other molecular species being measured in the sample is retrieved from calibration curves, described more fully in connection with FIG. 7, which are stored in the memory of the circuit. Alternatively, the proportion of molecular species in the gas sample may be determined by entering signal R into a calculation circuit 130 where a conventional algorithm is employed to calculate the proportion as described in connection with FIG. 8. The determined concentration of the molecular species is indicated on a readout 132 and if the proportion reaches an undesirably high level, an alarm 134 is activated.

A sensor is not required if the filters are arranged on the chopper at an interval other than 180°. For example, if they are separated by 135°, signals A, B, C and D are provided at 0°, 90°, 135° and 225°, respectively. This uneven spacing serves to identify the respective signals and eliminates the need for a sensor.

Figure 7:
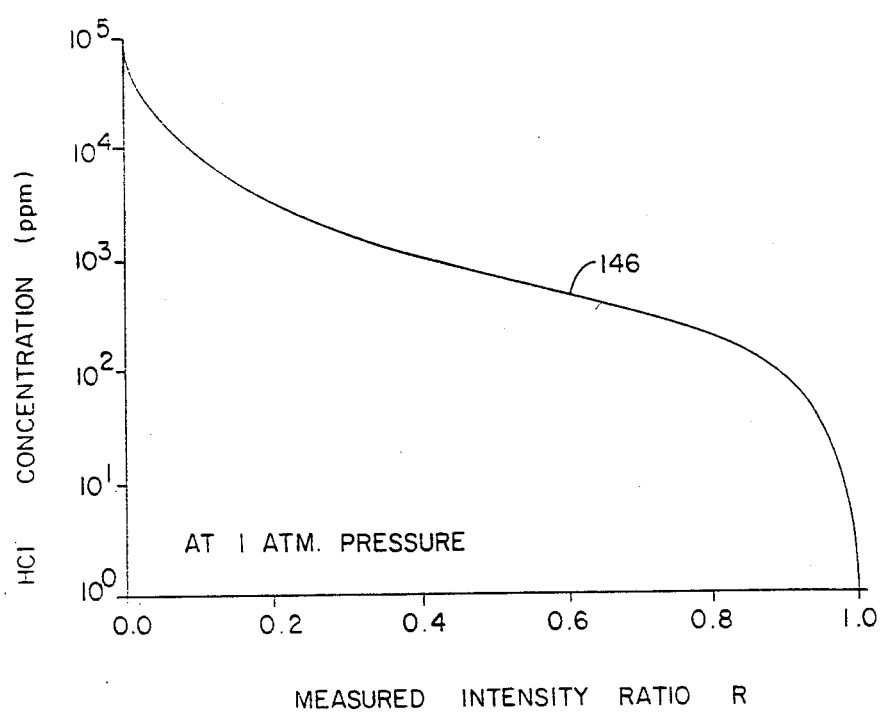
FIG. 7 illustrates the variation in the measured concentration of HCl under ambient sea level conditioning with variation in the ratio of the normalized detector intensities.

A calibration curve, such as is hown in FIG. 7, may be used by table retrieval circuit 128 for determining stored HCl concentration values. Values along the X axis represent the divider cicuit output signal R provided to the retrieval circuit 128. Values along the Y axis indicate the concentration of HCl in parts per million. These values are obtained in an HCl gas sample which is maintained at a constant temperature of 72° F. and pressure of one atmosphere. Similarly shaped curves, not shown, at different concentrations can be obtained at different temperatures and pressures. Each of these calibrated curves is compiled by employing a gas sample having known concentrations of HCl and predetermined temperatures and pressures and measuring values R for such samples.

Figure 8:
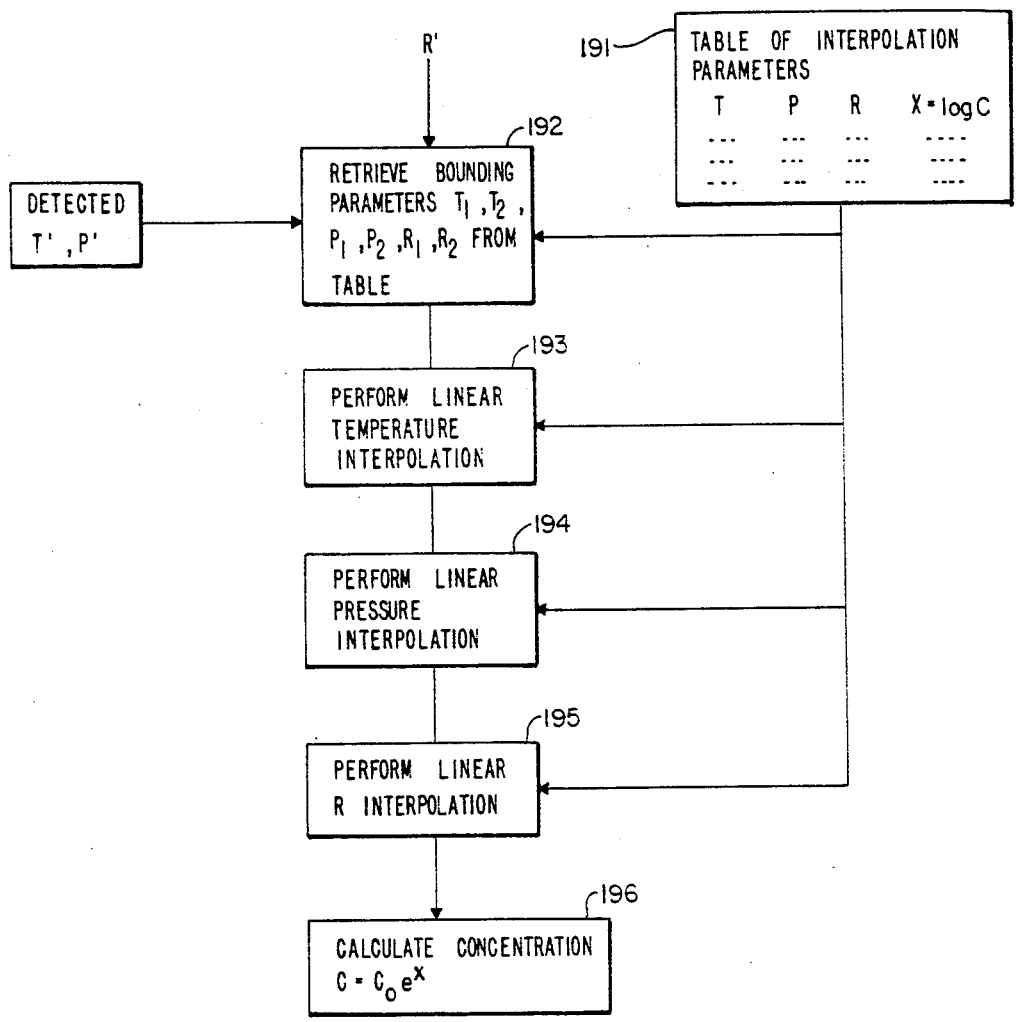
FIG. 8 is a flow chart for one method of resolving the proportion of molecular species in the sample gas.

Logic which may be employed in circuit 130 to calculate the proportion of trace element is shown in FIG. 8. Table 191 is provided with known combinations of values of temperature T, pressure P, ratio R and X, where X, a function of T, P and R equals the log of the concentrations C. Table 191 thus expresses the functional dependence of X on T, P and R. Known temperatures, pressures and R values $T_1$, $T_2$, $P_1$, $P_2$ and $R_1$, $R_2$ which bound the detected values T′, P′, and R′, respectively, are retrieved from Table 191 at step 192. These values are used to perform known 3-dimensional linear interpolation, steps 193, 194 and 195 to calculate the value of X which is associated with T′, P′ and R′. Concentration is calculated, step 196, by re-exponentiating X and multiplying $e^x$ by $C_0$ where $C_0$ is a typically constant predetermined scaling factor.

Figure 9:
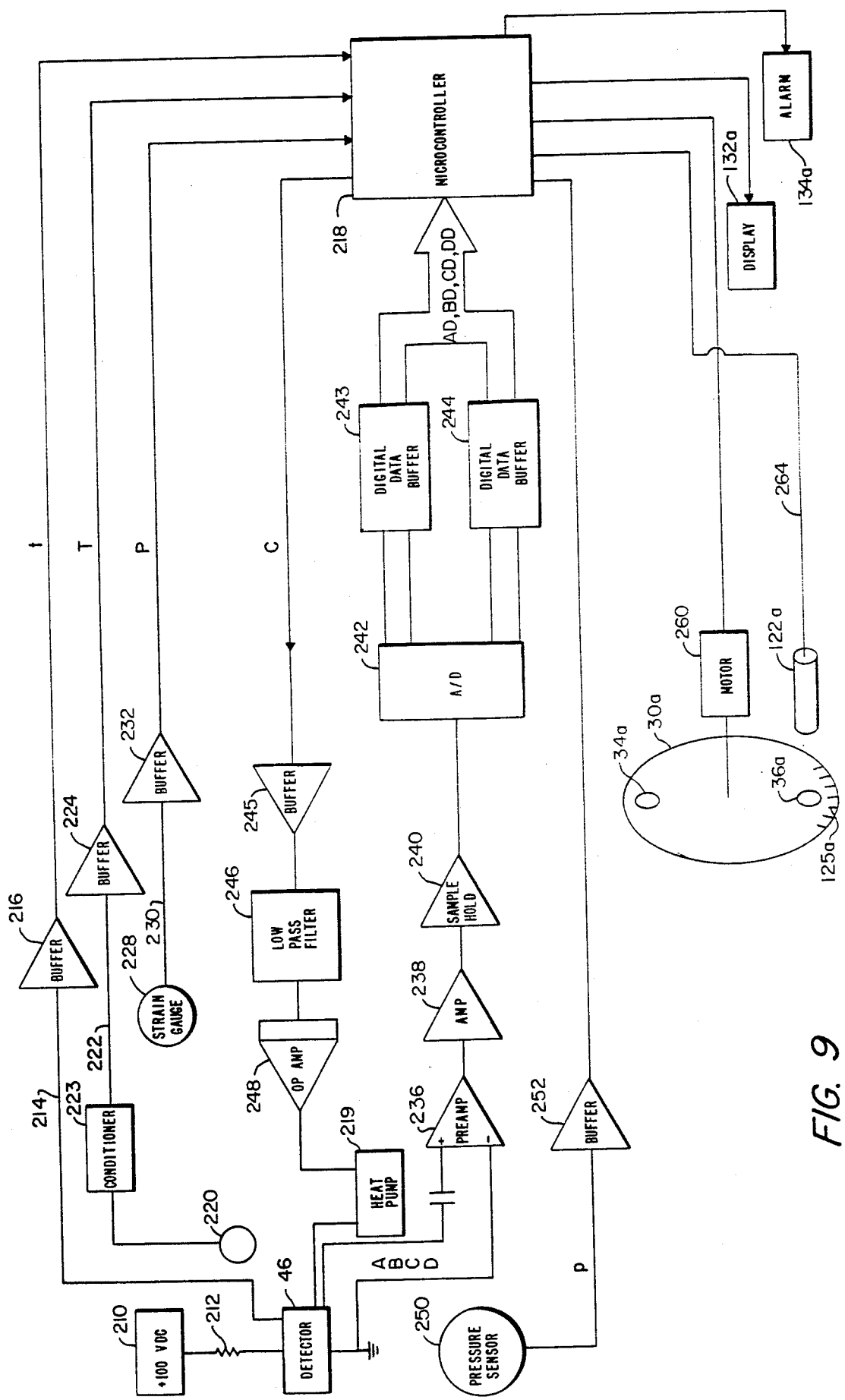
FIG. 9 is a schematic diagram of a preferred alternative signal processor which digitally processes the detected intensity signals to determine the proportion of molecular species in the gas sample.

In an altrrnative preferred embodiment the intensity signals alternatively may be processed digitally as shown in FIG. 9. Detector 46 is connected to a 100-volt bias supply 210 through a resistor 212. Because the noise and sensitivity of detector 46 is strongly temperature dependent the detector includes a thermistor which provides a temperature signal t over line 214 and through amplifier 216 to microcontroller 218. A thermocouple 220 measures the temperature of the incoming gas entering optical cell 12. Its signal T proceeds over line 222 through thermocouple signal conditioner 223 and amplifier 224 to microcontroller 218. A pressure transducer 228 detects the pressure of the incoming gas sample and provides a signal P representative of that pressure over line 230 and through amplifier 232 to the microcontroller.

The absorption signals A, B, C and D provided by detector 46 are amplified and buffered by a preamplifier 236 and then directed through an amplifier 238, a sample and hold circuit 240 and an A/D converter 242. The signals are then transmitted through digital data buffers 243, 244 to the input of microcontroller 218. As a result each signal A–D is converted to a respective, for example, fourteen bit digital signal AD, BD, CD, DD.

The microcontroller is programmed in a conventional manner to process the signals so that signal AD is normalized with respect to signal CD, signal BD is normalized with respect to signal DD and the normalized intensity signals are compared to provide a signal R, not shown. The steps of such a program may include, for example, the division steps performed by the divider circuits described in FIG. 6. The signal R derived in this manner is then employed in either a table retrieval or a calculation in microcontroller 218, which operate analogously to the description in FIGS. 7 and 8 to provide the detected proportion of trace element to display 132a. Alarm 134a sounds when the concentration exceeds a predetermined level.

In order to prevent the heat generated by motor 260 and the ambient environment from disrupting the concentration determination the detector may include and be cooled by a solid state heat pump 219. Microcontroller 218 reads detector temperature t and feeds back a control signal C through buffer 245, low pass filter 246 and power operational amplifier 248 which operates the heat pump when the detector temperature t is too high.

Again, the sample and reference beams of infrared radiation are chopped into their respective absorbing and nonabsorbing wavelength bands by a chopper wheel 30a. The wheel is driven by a motor 260 which is controlled by the microcontroller. Sensor 122a senses indicia 125a on the wheel and provides a signal to microcontroller 218 over line 264 which indicates to the microcontroller which signal AD–DD it is receiving.

Figure 10A:
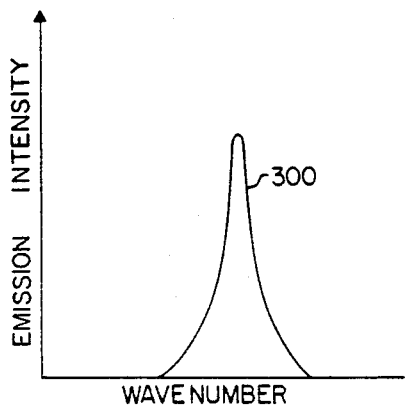
FIG. 10A illustrates a relatively narrow primary emission line for an infrared molecular species emission source.

The maximum resolvable concentration and sensitivity of the monitor may be adjusted by varying the size and shape of the absorbing emission lines. For example, as absorbing emission line 300, FIG. 10A, is passed through a gas sample in which the molecular species has a concentration of $C_1$, FIG. 10C, emission line 300 is somewhat absorbed by the molecular species in the gas, e.g., absorption line $C_1$ reduces emission line 300, and its resulting output intensity is 300a, FIG. 10D. Passing emission line 300 through a sample having a larger concentration $C_2$, FIG. 10C, of the molecular species results in an even smaller output intensity, 300b, FIG. 10D. As the concentration of the molecular species increases the output intensity of the absorbing emission line becomes smaller until with a concentration of greater than $C_3$, e.g., with a concentration of $C_4$ or $C_5$, absorbing emission line 300 is almost entirely absorbed and the output intensity for the emission line at these concentrations is harder to detect. See the detected intensity ratio line 301, FIG. 10F. With the absorbing emission line of the width and intensity of line 300 it is therefore impossible to detect concentration differences between $C_4$ and $C_5$ or, indeed, to detect any higher levels of concentration.

Figure 10B:
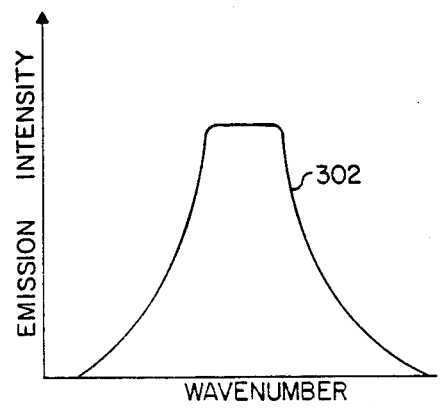
FIG. 10B illustrates a wider primary emission line resulting from, for example, an increased concentration of HCl.
Figure 10C:
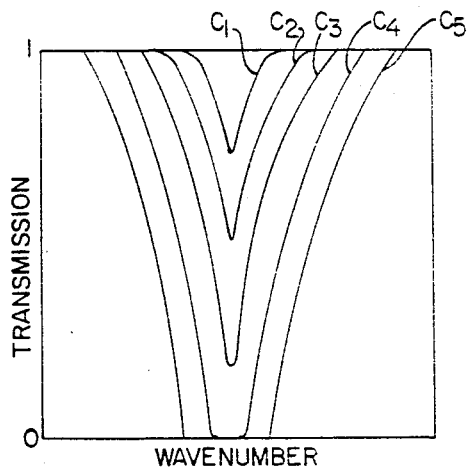
FIG. 10C illustrates at increasing respective sample concentrations the absorption lines corresponding to the emission line of FIGS. 10A and 10B for a sample containing the molecular species being monitored.
Figure 10D:
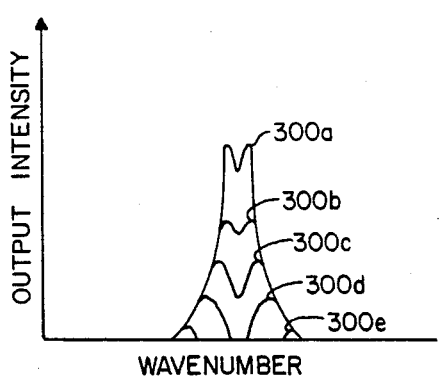
FIG. 10D illustrates the respective output intensities of the primary emission line of FIG. 10A after it passes through samples having the molecular species concentrations of FIG. 10C.
Figure 10E:
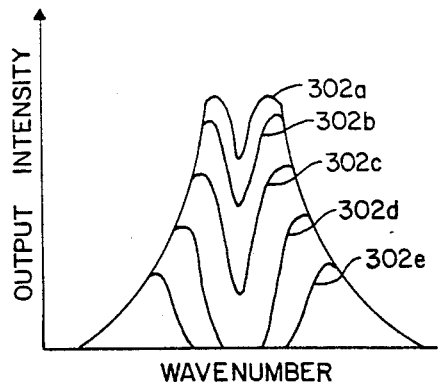
FIG. 10E illustrates the respective output intensities of the primary emission line of FIG. 10B after it passes through samples having the molecular species concentrations of FIG. 10C.

To improve concentration measurements at relatively high concentrations, it is advantageous to increase the concentration of the molecular species of interest in the emission source so that a broader emission line 302, FIG. 10B, which corresponds to the position of line 300, is provided. The line may also be broadened by similarly increasing the path length, or by increasing the pressure, varying the temperature or changing the concentration of the diluting gas in the emission cell. As broadened line 302 is passed through a gas sample having a molecular species concentration of $C_1$, FIG. 10C, the molecular species in the sample absorbs a portion of line 302 and an output intensity of 302a, FIG. 10E, is provided. At each higher concentration level, e.g., $C_2$, $C_3$, $C_4$ and $C_5$, progressively more of emission line 302 is reduced as shown by curves 302b–e. However, even at the very high concentration level of $C_5$ a discernable output signal 302e is provided. As shown by line 303, FIG. 10F, the intensity signal does not drop to zero and measurements at very high concentrations can be made.

Figure 10F:
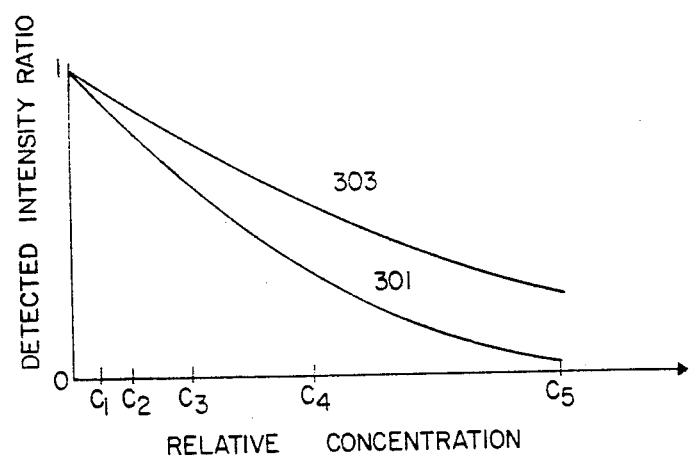
FIG. 10F illustrates for FIG. 10D the variation in output intensity with variation in concentration.

The disadvantage of empoying a relatively wide signal lies in that it is not as sensitive as the narrow signal. For example, as shown in FIG. 10F, when a wide emission line 302 is used at very low concentrations (below $C_1$) there is a smaller change in the output intensity. As a result, it may become quite difficult to distinguish the increasingly smaller concentrations from one another. On the other hand, employing the narrower absorbing emission line 300 of FIG. 10A provides a significantly greater change in intensity as the concentration is reduced below $C_1$. Increasingly smaller concentrations can be distinguished and as a result, enhanced sensitivity is provided. Accordingly, narrow emission lines should be employed when such sensitivity is required.

In alternative embodiments the maximum resolvable concentration may be improved by utilizing a larger number of absorbing emission lines.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. An infrared species specific emission source comprising:
   a closed container having at least one portion which is transparent for containing at least one specific gas phase molecular species; and
   an electric coil for heating the molecular species within said container sufficiently to cause said species to emit a characteristic infrared spectral emission through said at least one transparent portion for said container to an infrared detection instrument.

2. The infrared emission source of claim 1 further including a housing for receiving said container and said electric coil.

3. The infrared emission source of claim 2 in which said housing includes insulation means for reducing heat loss from said container.

4. The infrared emission source of claim 3 in which said insulation means includes insulating material which surrounds at least a portion of said container and said electric coil.

5. The infrared emission source of claim 4 in which said electric coil is disposed about said container and further including means attached to said insulating material for mounting said electric coil about said container.

6. The infrared emission source of claim 5 in which said means for mounting includes a potting compound in which said electric coil is embedded.

7. The infrared emission source of claim 3 in which said insulation means includes a transparent insulating element spaced from a said transparent portion for transmitting the spectral emission therethrough.

8. The infrared emission source of claim 2 in which said housing includes heat dissipating means for maintaining said source at a substantially constant operaing temperature.

9. The infrared emission source of claim 1 further including means for maintaining said source at a substantially constant operating temperature.

10. The infrared emission source of claim 1 in which said container contains a combination of molecular species.

11. An emission source and target sample system for an infrared detection system comprising:
    a sample path for containing a target sample to be monitored for a selected molecular species; and
    an electric coil for heating a second selected molecular species within a closed container; for providing to said sample path an infrared species specific spectral emission source which corresponds to the absorption spectrum of the selected molecular species to be monitored.

12. The system of claim 11 further including a housing for receiving said container and said electric coil.

13. The system of claim 12 in which said housing includes insulation means for reducing heat loss from said container.

14. The system of claim 13 in which said insulation means includes insulating material which surrounds at least a portion of said container and said electric coil.

15. The system of claim 14 further including means attached to said insulating material for mounting said electric coil about said container.

16. The system of claim 15 in which said means for mounting includes a potting compound in which said heating element is embedded.

17. The system of claim 13 in which said insulation means includes a transparent insulating element spaced from a said transparent portion for transmitting the spectral emission spectrum therethrough.

18. The system of claim 12 in which said housing includes heat dissipating means for maintaining said source at a substantially constant operating temperature.

19. The system of claim 11 further including means for maintaining said source at a substantially constant operating temperature.

20. An emission source for an infrared detection system for measuring the presence of at least one gas phase molecular species in a gas sample comprising: means for providing to said gas sample an infrared species specific spectral emission source of the selected molecular species to be monitored including a closed container having at least one portion which is transparent for containing molecular species of the type to be monitored in the sample and an electric coil for heating the molecular species within the container sufficiently to cause said species to emit a characteristic infrared spectral emission through the at least one said transparent portion of said container.

* * * * *

UNITED STATES PATENT AND TRADEMARK OFFICE
CERTIFICATE OF CORRECTION

PATENT NO. : 4,780,613

DATED : October 25, 1988

INVENTOR(S) : Berstein et al

It is certified that error appears in the above-identified patent and that said Letters Patent is hereby corrected as shown below:

Column 1, before the "Field of Invention", add the following:

--The invention was made with Governmental support under
  F04704-84-C-0312 awarded by the Department of Defense.
  The Government has certain rights in the invention.--

Signed and Sealed this

Seventeenth Day of March, 1992

Attest:

HARRY F. MANBECK, JR.

*Attesting Officer*  *Commissioner of Patents and Trademarks*